United States Patent
Ehteshami et al.

(10) Patent No.: US 11,918,480 B2
(45) Date of Patent: *Mar. 5, 2024

(54) CERVICAL CAGE

(71) Applicant: Additive Implants, Inc., Phoenix, AZ (US)

(72) Inventors: John R. Ehteshami, Paradise Valley, AZ (US); Mahyar Zoghi, Phoenix, AZ (US)

(73) Assignee: Additive Implants, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,765

(22) Filed: Jul. 21, 2022

(65) Prior Publication Data
US 2023/0024730 A1 Jan. 26, 2023

Related U.S. Application Data

(63) Continuation of application No. 17/339,105, filed on Jun. 4, 2021, now Pat. No. 11,406,509.

(51) Int. Cl.
*A61F 2/44* (2006.01)
*A61F 2/30* (2006.01)

(52) U.S. Cl.
CPC ......... *A61F 2/442* (2013.01); *A61F 2/30771* (2013.01); *A61F 2002/30471* (2013.01); *A61F 2002/30518* (2013.01); *A61F 2002/30841* (2013.01); *A61F 2002/30934* (2013.01)

(58) Field of Classification Search
CPC ... A61F 2/442; A61F 2/4425; A61F 2002/443
See application file for complete search history.

(56) References Cited

U.S. PATENT DOCUMENTS

| | | | |
|---|---|---|---|
| 10,925,749 B2 * | 2/2021 | Ledet | A61F 2/44 |
| 2001/0016774 A1 * | 8/2001 | Bresina | A61F 2/442 623/17.15 |
| 2008/0161919 A1 * | 7/2008 | Melkent | A61F 2/442 623/17.11 |
| 2015/0100125 A1 * | 4/2015 | Protopsaltis | A61F 2/4455 623/17.15 |
| 2021/0236297 A1 * | 8/2021 | Sanders | A61F 2/447 |

* cited by examiner

*Primary Examiner* — Matthew J Lawson
(74) *Attorney, Agent, or Firm* — Snell & Wilmer L.L.P.

(57) ABSTRACT

The present invention relates to an implantable cervical cage having a flexible posterior plate allowing for posterior displacement or movement of the cage.

20 Claims, 7 Drawing Sheets

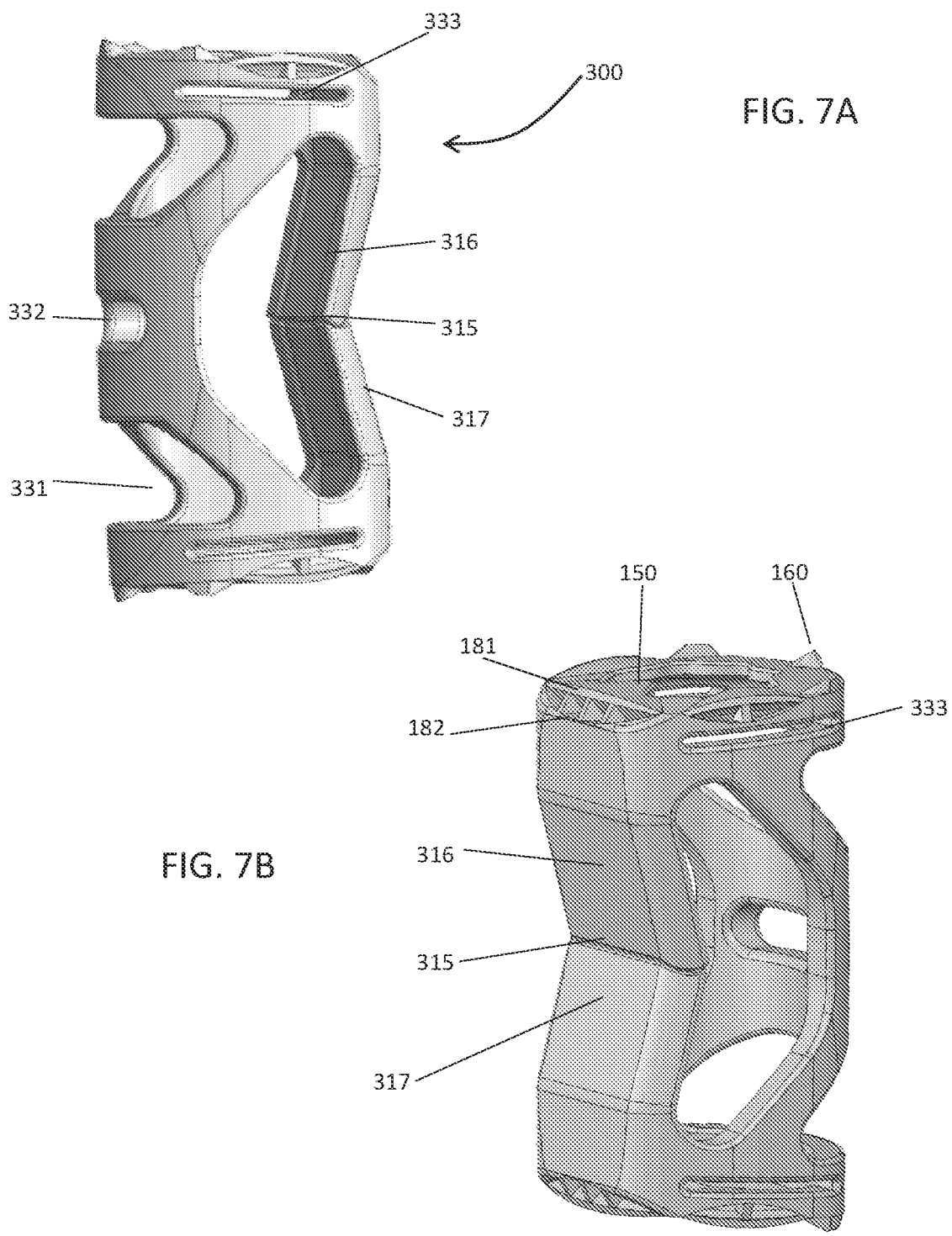

CERVICAL CAGE

CROSS-REFERENCE TO RELATED APPLICATIONS

This application is a continuation of, claims priority to, and the benefit of, U.S. patent application Ser. No. 17/339,105 filed on Jun. 4, 2021, which is entitled "CERVICAL CAGE." The contents of the above-identified application is herein incorporated by reference in its entirety.

FIELD OF THE INVENTION

The invention relates to orthopedic implants and is more particularly related to intervertebral implants.

BACKGROUND OF THE INVENTION

The human spinal column has more than twenty discrete bones sequentially coupled to one another by a tri-joint complex that consists of an anterior disc and two posterior facet joints, the anterior discs of adjacent bones being cushioned by cartilage spacers referred to as intervertebral discs. The more than twenty bones are anatomically categorized in one of four classifications: cervical, thoracic, lumbar, or sacral. The cervical portion of the spine extends from the base of the skull and includes the first seven vertebrae. The intermediate twelve vertebrae make up the thoracic portion of the spine. The lower portion of the spine comprises five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in dose proximity. In spite of these complications, the spine is a highly flexible structure, capable of a high degree of curvature and twist in nearly every direction.

A corpectomy is a surgical procedure wherein a portion of the vertebral body and adjacent intervertebral discs are removed to relieve pressure or decompress the spinal cord, thecal sac, and nerves. The procedure is generally performed through an anterior or lateral approach, and less commonly through a posterior approach. A structural system needs to be put in place in the space created by removal of the bone and accompanying disc material. This structural system has historically been a fibular allograft cut to size placed between two distracted endplates of the adjacent vertebras. These grafts were later partially replaced with a device generally referred to as a corpectomy cage.

The intervertebral disc disposed between the vertebrae in the human spine has a peripheral fibrous shroud (the annulus) that surrounds a spheroid of flexibly deformable material (the nucleus). The nucleus comprises a hydrophilic, elastomeric cartilaginous substance that cushions and supports the separation between the bones. The nucleus also permits articulation of adjacent vertebral bones relative to one another to the extent such articulation is allowed by the other soft tissue and bony structures surrounding the disc. The additional bony structures that define pathways of motion in various modes include the posterior joints (the facets) and the lateral intervertebral joints (the unco-vertebral joints). Soft tissue components, such as ligaments and tendons, constrain the overall segmental motion as well.

Traumatic, genetic, and long-term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

The corpectomy cage is used to fill the space created by the tissue removal, to transmit loads and to provide a scaffolding for bone to grow across the adjacent vertebral bodies. The cage is subject to loads and torques in all six degrees and needs to maintain its position for the fusion process to occur. This corpectomy cage can work with integrated bone anchors, and or, supplemental fixation in the form of anterior or lateral plate and screws, or lateral and or posterior rods and screws.

Two types of cages are generally available: A static fixed height cage and an expandable cage. Static cages are manufactured in various heights so that one cage can be selected to best fit the cavity created by the removed vertebral body. Cages may also be modular such that the upper and lower portions may be separably connectable. The upper and lower portions may be of different sizes and shapes. Various uppers and lowers may be assembled to create cages of desired heights. The ability to combine modular uppers and lowers allows for more streamlined manufacturing, inventory, and distribution. Alternatively, an expandable cage having a variable height can be used to maintain spacing of the vertebrae above and below the removed body material. Such expandable cages typically include telescoping members with a physical mechanism to retain the members at the selected height. For example, telescoping members are formed with threaded or ratcheting interconnections, or the use of pins, set screws and the like, to fix the members at a selected height. Expandable cages may be modular as described above to reduce the need for inventory.

Both types of cages have limitations and problems. Fixed cages have excellent structural integrity but are cumbersome to place. The fixed cage must be the correct height. Producing a range of cages to include many possible height requirements also creates a demand on manufacturing and inventory maintenance. Otherwise, if the cage is too big, it can cause over distraction of the vertebral bodies or damage the vertebral body above and below the cage. If the cage is too small, it can move out of position. Expandable cages are generally easier to place and size correctly. However, the mechanical mechanism used to expand the cage may fail in vivo, which can lead to catastrophic results. The telescoping members are weight bearing so as to support the axial loads on the cage when the cage is implanted. Thus, the strength of the cage depends upon the inner connection between the telescoping members. Additionally, expandable cages compromise the amount of space available for packing of bone graft to accommodate the expanding mechanism; thus, resulting in decreased bone graft volume compared to static cages. Cages have also been made with integrally fixated bone anchors to secure them to the adjacent endplates. These cages both static and expandable can be manufactured in metals and polymers, with or without integral fixation. Often, the fixation is generally located in and through the anterior portion of the cage.

Subsidence of the implant is a complex issue and has been attributed to many factors. Some of these factors include aggressive removal of the endplate; an implant stiffness significantly greater than the vertebral bone; smaller sized implants which tend to sit in the center of the disc space against the weakest region of the endplates; and implants with sharp edges which can cause localized stress fractures in the end-plates at the point of contact. The most common solution to the problem of subsidence is to choose a less stiff implant material. This is why PEEK and cadaver bone have become the most common materials for spinal fusion implants. PEEK is less stiff than cortical bone, but more stiff than cancellous bone. PEEK is a preferred choice for loading bone graft within an implant. In accordance with Wolfe's Law, the bone graft within the implant should be loaded in order for it to convert to living bone tissue. Living bone bridging from one vertebral body through the spacer and joining with the second vertebral body is the definition of "interbody fusion" which is one the primary goals of an ACDF procedure.

Independent of the type of corpectomy cage or allograft, there are particular failures that occur called "kicking out." The corpectomy cage or allograft dislodges from the position it was placed at the time of the surgery kicking out anteriorly or posteriorly. This occurs when the fibular allograft or corpectomy cage is used with no fixation or anterior only supplemental fixation such as a plate and screws. The high rates of such failures have led most surgeons to perform additional posterior fixation which significantly decreases the complication rate. It is believed that that reason corpectomy cages and fibular allograft "kick out" without supplemental posterior fixation is that the length of the posterior column changed during flexion and extension particularly in the cervical spine which has greater range of motion in flexion and extension. This change in the posterior column height leads to variable loading scenarios on the corpectomy cage or fibular allograft, which can lead to "kicking out." Significant attempts to improving anterior plate and screw fixation have done little to solve this problem that can lead to catastrophic failure. The best solution has been supplemental posterior fixation, which requires doing a second surgery from the back of the neck.

A supplemental posterior fixation limits the length of the posterior cervical column. The combination of anterior and posterior columns stabilizes both the anterior and posterior column height and minimize the changes relative to the opposing vertebral endplates being fused. The stabilization of the columns incurs the significant cost and burden of requiring an additional surgery through the posterior of the spine. The additional surgery adds significant financial expense and health burdens to the operation including additional surgical time and increased risk of complications like infection and posterior muscle denervation.

The objective of the present invention is a novel corpectomy cage design which substantially overcomes the problems of the prior art, which necessitates a combined anterior and posterior operation. By having a corpectomy cage with different stiffnesses in the anterior side and the posterior side, the cephalad and caudal portions of the cage that rest against the adjacent endplates can rotate along the transverse plane. This allows the cage to maintain uniform contact with end plates when flexion and extension motions occur in the sagittal plane; thereby, preventing "kick out."

Further by providing a spring like structure the corpectomy cage can provide decrease stiffness to loads preventing subsidence into adjacent endplates.

Further by manufacturing such an implant with 3D printing technology a significant cost savings can be obtained.

Further, a combination of such a dynamic cage in both static or expandable forms with or without integral fixation can decrease the need for supplemental posterior fixation. There by significantly lowering operative cost and surgical time and complication rates associated with a second stage surgery.

These and other objectives will become apparent from the following description of the invention.

SUMMARY OF THE INVENTION

In an embodiment, a cervical cage may include a superior end plate, with an anterior side and posterior side, and a superior perimeter connecting the anterior and posterior sides. The cervical cage further may include an inferior end plate, with an anterior side and a posterior side, and an inferior perimeter connecting the anterior and posterior sides. The superior end plate and the inferior end plate may define a central region therebetween. The central region may be further defined by an anterior plane extending between the superior anterior side and the inferior anterior side, and a posterior plane extending between the superior posterior side and the inferior posterior side. The central region may further include a longitudinal axis extending through the central region between the superior end plate and the inferior end plate. The cage further includes an anterior support connecting the superior end plate and the inferior end plate and extends along an anterior plane between the superior anterior side and the inferior anterior side. The cage further includes a posterior support connecting the superior end plate and the inferior end plate at the posterior edges. The posterior support may be configured for controlled movement, wherein the controlled movement causes the posterior plane to shorten. The posterior support may also comprise a superior end connected to the superior posterior side on the posterior plane and an inferior end connected to the inferior posterior side on the posterior plane The cervical cage further includes an extension between the superior and inferior end.

The extension may deviate from the posterior plane. The deviation may be anterior from the posterior plane and into the central region or the extension may deviate posteriorly from the posterior plane.

The extension may have at least one apex anteriorly or posteriorly to the posterior plane. The extension may be curved. The at least one apex may be situated anywhere in the central region. The at least one apex may be positioned closer to the longitudinal axis than the posterior plane between the superior and inferior posterior sides, or the apex may be positioned closer to the posterior plane than the longitudinal axis. The apex may be positioned closer to the superior end plate than the inferior end plate, or the at least one apex may be positioned closer to the inferior end plate than the superior end plate. The superior end plate may include at least one recess and/or the inferior end plate may include at least one recess.

In an embodiment a spinal implant may include a caudal portion, with an caudal anterior side and a caudal posterior side, and a caudal perimeter connecting the anterior and posterior sides. The cage may have a cephalad portion, with a cephalad anterior side and a cephalad posterior side, and a cephalad perimeter connecting the anterior and posterior sides. The caudal and cephalad portions may define an intermediate region therebetween and are connected by first and second walls. The first wall may extend between the caudal anterior side and the cephalad anterior side. The second wall may extend between the caudal posterior side and the cephalad posterior side. The caudal anterior side and the cephalad anterior side may be separated by an anterior distance along an anterior plane. The caudal posterior side and the cephalad anterior side may be separated by a posterior distance along a posterior plane. The second wall may be configured to have a preferential movement and/or displacement between the cephalad and the caudal portions.

The preferential movement and/or displacement may reduce the posterior distance. The second wall may extend between the caudal posterior side and the cephalad posterior side and anteriorly to the posterior plane.

The second wall may extend between the caudal posterior side and the cephalad posterior side and posteriorly to the posterior plane.

The second wall may extend between the caudal posterior side and the cephalad posterior side anteriorly and posteriorly to the posterior plane.

In an embodiment, a spinal implant may include a superior end plate, having an anterior side and a posterior side, and a superior perimeter connecting the anterior and posterior sides. The implant may include an inferior end plate, with an anterior side and posterior side, and an inferior perimeter connecting the anterior and posterior sides. The superior and inferior end plates may define a central region therebetween. The central region further may be defined by an anterior plane and a posterior plane extending between each of the anterior and posterior side. The implant may include an anterior support connecting the superior end plate and the inferior end plate. The implant may include a posterior support connecting the superior end plate and the inferior end plate. The posterior support may have a greater flexibility than the anterior support and the posterior support may be configured for a displacement in a preferred direction.

When the posterior support flexes it may traverse a posterior plane extending between the superior end plate and the inferior end plate in a posterior direction. When the posterior support flexes it may traverse a posterior plane extending between the superior end plate and the inferior end plate in an anterior direction. When the posterior support flexes it may traverse a posterior plane extending between the superior end plate and the inferior end plate in a posterior direction and an anterior direction.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

FIG. 7A shows a side anterior perspective of a cervical cage with a hinged posterior.

FIG. 7B shows a side posterior perspective of a cervical cage with a hinged posterior.

DETAILED DESCRIPTION OF THE INVENTION

Figure 1:
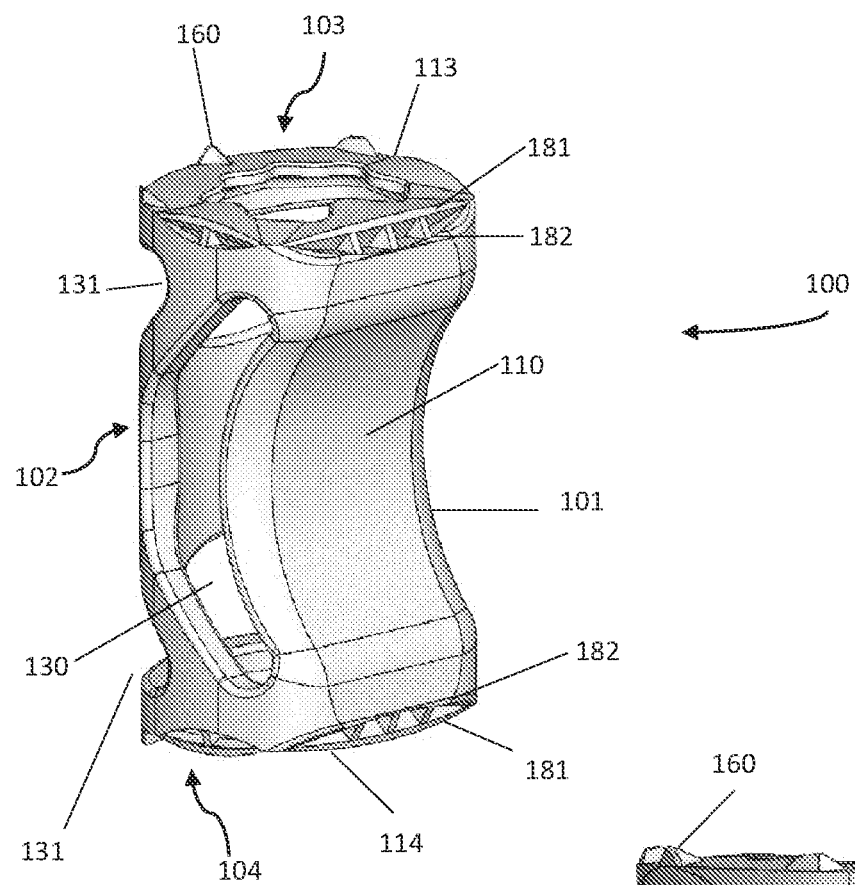
FIG. 1 shows a posterior perspective of a cervical cage.

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 7, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The term "adjacent" refers to items that are physically near or next to one another and may or may not be in physical contact. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard anatomical reference planes and spinal terminology are used in this specification with their customary meanings.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

FIGS. 1-4 illustrate by way of example only, a cervical cage 100 for implantation between two adjacent vertebral bodies. The implant 100 has dimensions of height, width, and length suitable for placement between vertebral bodies. In this example, the height extends along a cephalad-caudal direction, the width extends along a right-left direction, and the length extends along an anterior-posterior direction. The cervical cage implant 100 may be made of any suitable biocompatible material. Various biocompatible materials contemplated include, but are not limited to, poly-ether-ether-ketone (PEEK), other polymers including bioresorbable polymers, ceramics, composites, bone or bone substitute materials, and biocompatible metals including stainless steel, titanium, or tantalum and their alloys. The cage 100 may also include multiple and combinations of the materials. The cage 100 may be manufactured by known methods such as machining, molding, forming, or 3D printing. The cage 100 may be provided in any number of shapes or sizes depending on the specific surgical procedure, need, or patient anatomy. The cage 100 may contain separate radiographic markers of any size of shape suitable to facilitate effective and accurate visualization of implant placement, necessary depending on the base material of the implant.

As shown in FIG. 1, the cage 100 includes a posterior side 101 opposite and anterior side 102, atop side 103 opposite a bottom side 104. The cage 100 generally has a vertical axis that runs from the top side 103 to the bottom side 104. The posterior 101, anterior 102, top 103, and bottom 104 sides generally contain a central space. The central space may be an open void or a low-density and compressible material. The central space may be large enough so that the cage may be effectively hollow.

The cage 100 includes a flexible posterior plate 110, an anterior plate 112, a top plate 113, and a bottom plate 114. The top plate 113 is bounded by a top perimeter 123 and connected by a side support 133. The bottom plate 114 is bounded by a bottom perimeter 124 and connected by a side support 133. The anterior plate 112 is connected to an anterior side of the top perimeter 123 and an anterior side of the bottom perimeter. A posterior plane is created spanning between where the posterior plate 110 connects to the top plate 113 and the bottom plate 114. An anterior plane is created spanning between where the anterior plate 112 connects to the top plate 113 and the bottom plate 114.

FIG. 1 shows the posterior plate 110 having a curvature deviating from the posterior plane in an anterior direction. The posterior plate 110 is shown with a constant gradual curvature into the central space, with an apex generally centered in the space and the central axis. However, the apex may exist in any configuration in locations anterior of the posterior plane. Alternative locations, relative to a central axis, include points more anterior or posterior of the axis, and points closer to the top plate 113 or bottom plate 114. The posterior plate 110 may have a non-regular curvature or have multiple apexes at different locations within the central space. FIG. 1 depicts the posterior plate 110 as having a lateral width similar to the width of the cage 100. However, the posterior plate 110 may have varying widths greater than or less than the width of the cage 100. The width of the posterior plate 110 may be uniform along the height, between the top plate 113 and the bottom plate 114, or the posterior plate 110 may have varying widths along the height. The posterior plate 110 may have various thicknesses across the plate 110.

Although not shown, the posterior plate may also extend posterior of the posterior plane, away from the central space and central axis of the cage 100. Similar to the posterior plate 110 in FIG. 1, a posteriorly extending posterior plate 110 may have a constant gradual curvature away from the central space, with an apex generally centered relative to the cage 100 and the central axis. However, the apex may exist in any configuration in locations posterior of the posterior plane. Alternative locations, relative to the central axis, include points closer or further away from the axis and posterior plane, and points closer to the top plate 113 or bottom plate 114. The posterior plate 110 may have a non-regular curvature or have multiple apexes at different locations posterior from the posterior plane and the cage 100. The posterior plate 110 as having a lateral width similar to the width of the cage 100. However, the posterior plate 110 may have varying widths greater than or less than the width of the cage 100. The width of the posterior plate 110 may be uniform along the height, between the top plate 113 and the bottom plate 114, or the posterior plate 110 may have varying widths along the height. The posterior plate 110 may have various thicknesses across the plate 110.

Figure 2:
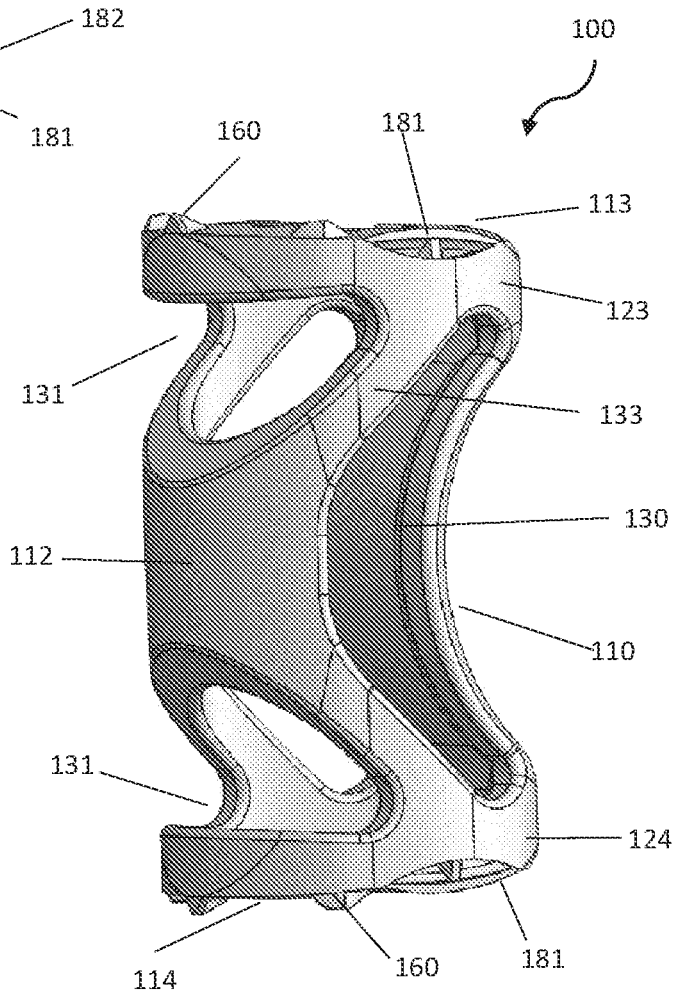
FIG. 2 shows an anterior perspective of a cervical cage.
Figure 3:
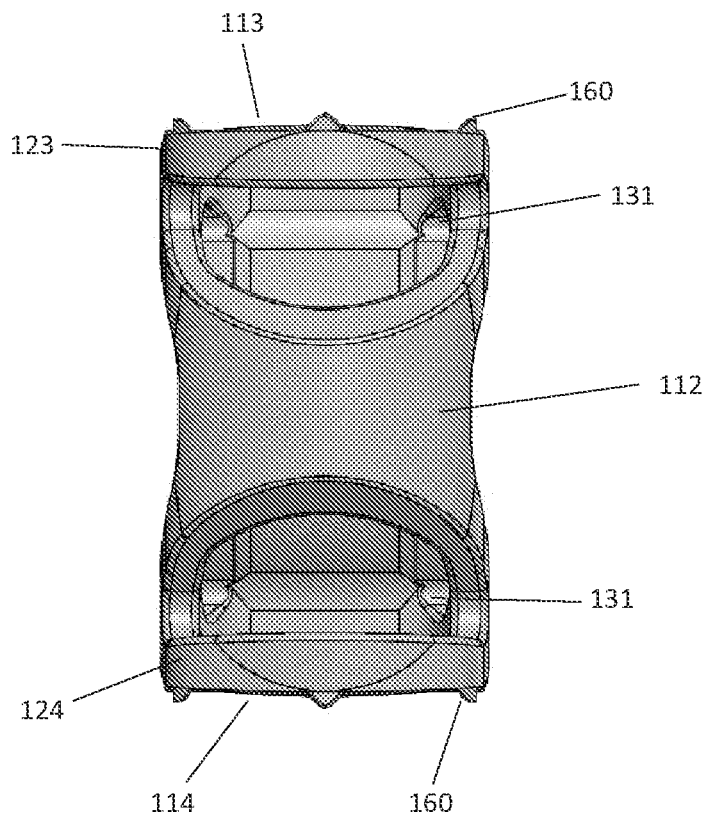
FIG. 3 shows an anterior view of a cervical cage.
Figure 4:
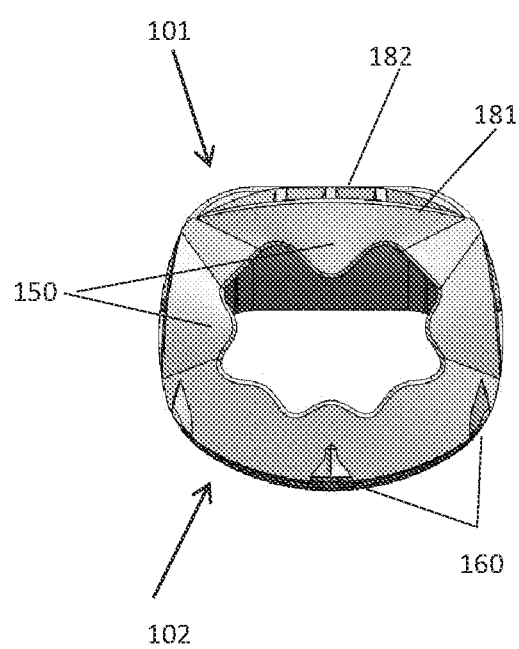
FIG. 4 shows a top view of a cervical cage.

FIGS. 2 and 3 show the anterior side 102 of the cage 100 and the anterior plate 112. The anterior plate 112 is configured to provide a more rigid structure to the anterior side 102 of the cage 100. The anterior plate 112 is shown connected to lateral edges of the top plate 113 and the bottom plate 114, but the anterior plate may connect to the cage 100 and the top 113 and bottom plates 114 in any configuration that provides proper stability of the cage 100. The illustrated configuration of the anterior plate 112 in FIGS. 2 and 3 provide side apertures 130 and anterior apertures 131. The apertures 130 131, as well as the central space, may allow for bone ingrowth, weight reduction, and space for displacement of the posterior plate 110, top plate 113, bottom plate 114, and the lobe 150. FIG. 4 shows an anterior perspective of the cage 100 and a configuration of the anterior plate 112 and how it connects to the top and bottom perimeters 123 and 124.

Figure 5A:
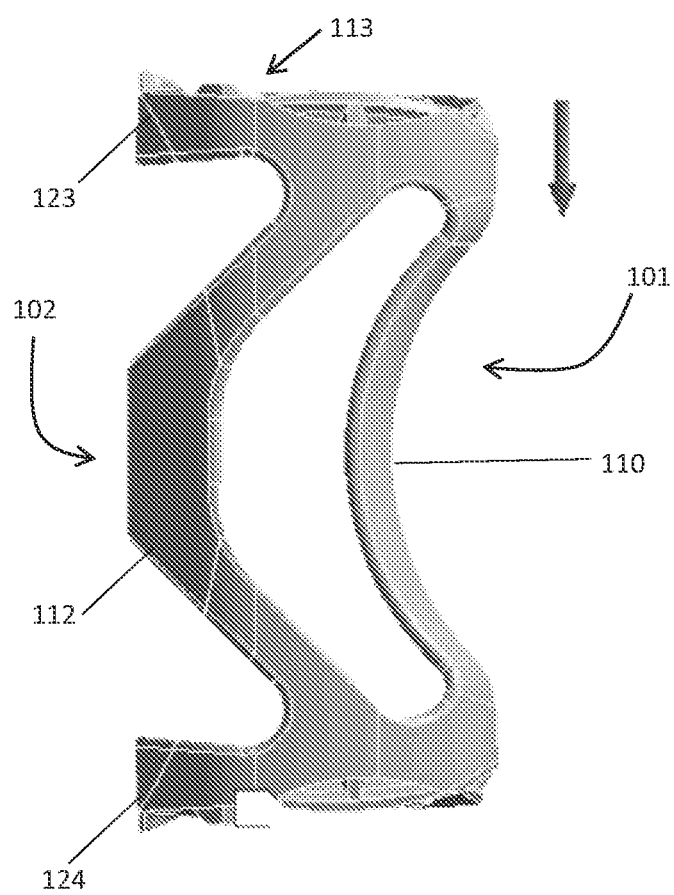
FIG. 5A shows a side view of a cervical cage in a relaxed state.
Figure 5B:
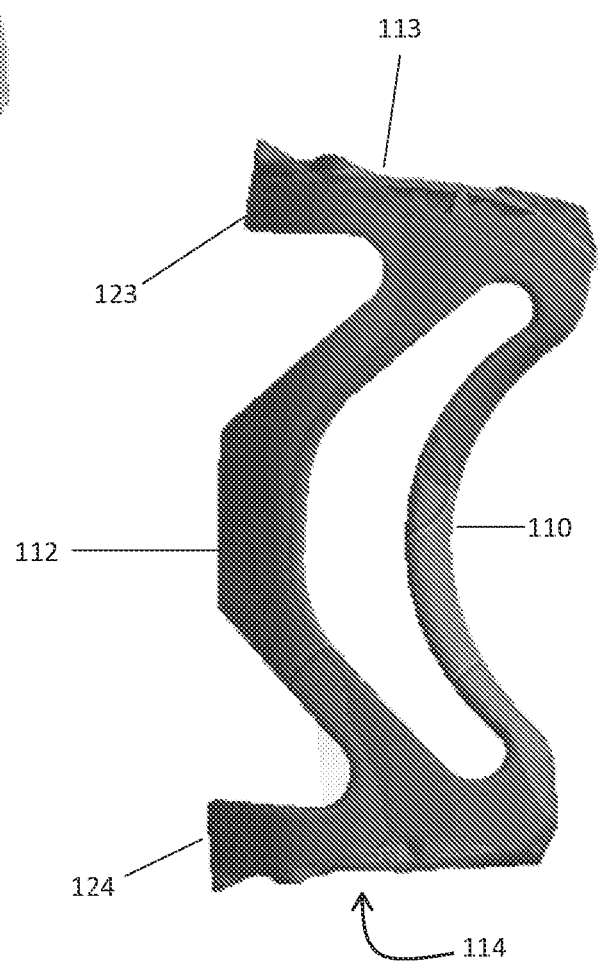
FIG. 5B shows a side view of a cervical cage in a flexed state.

The shape, design, and configuration of the posterior plate 110 allows the posterior side 101 of the cage to deflect so that the top plate 113 and the bottom plate 114 to transition toward each other at the posterior sides of the top perimeter 123 and the bottom perimeter 124, along the posterior plane. The anterior plate 112 restricts the movement of the anterior side of the top plate 113 and the bottom plate 114 toward one another along the anterior plane. Referring to FIGS. 5A and 5B, the amount and direction of deflection is shown. FIG. 5A represents a first or relaxed state of the cage 100, in which the posterior plate 110 is in a non-tensioned or non-flexed state. The posterior portion of the top plate 113 is approximately the same distance from the posterior portion of the bottom plate 114 as the anterior portion of the top plate 113 is from the anterior portion of the bottom plate 114. FIG. 5B represents a second or flexed state of the cage 100, in which the posterior plate 110 is under stress and compressed or flexed. The curvature of the posterior plate 110 allows the reduction in distance between the posterior portion of the top plate 113 and the bottom plate 114. Any change between the anterior portion of the top plate 113 and the anterior portion of the bottom plate 114 is incidental. The configuration of the anterior plate 112 and the connection points at the top perimeter 123 and bottom perimeter 124 may be tuned to allow or prevent any subsequent movement of the anterior side 102 of the cage 100. As shown in FIGS. 5A and 5B, the anterior apertures 131 do not prevent slight movement of the anterior side 102 of the top plate 113 and the bottom plate 114.

In practice, the ability of the posterior side 101 of the cage 100 to flex or compress, allows a patient with an implanted cage 100 to more easily look up. The posterior plate 110 absorbs non-centralized force, thus reducing the opportunity for subsidence of the cage 100 anteriorly. The movement of the cage 100 may also be described as a change of displacement of the posterior side, relative to the anterior side. The posterior plate 110 may bends or displace in any direction that the structure passively or actively allows. The structural design of the posterior plate 110 creates a preferential direction for displacement. As discussed above the posterior plate 110 may have a curvature or initial displacement, in the first or relaxed state, from the posterior plane 101. The structural design in the first state allows the posterior plate 110 to experience a controlled bending in the preferential direction. In FIGS. 5A and 5B, the preferential direction is anterior, or toward the center of the cage 100. It is envisioned that the cage 100 may have a first state in which the posterior plate 110 deflects posteriorly, so that the preferential direction is also posterior. Other embodiments may be created by designing the posterior plate 110 to have a medial or lateral first state, so that the preferential bending direction also may be medial or lateral.

As shown in FIG. 4, the top plate 113 and the bottom plate 114 have at least one lobe 150 or extension, extending from the perimeters 123 and 124 towards the central axis of the cage 100. The lobes 150, may function as a cantilever-a structural element anchored at one end to a support, from which it protrudes. Lobes and cantilevers are discussed in U.S. Pat. No. 10,299,938, which is incorporated herein by reference. When subjected to a structural load, the cantilever carries the load to the support. The lobe is structured to extend from a base to at a terminus. As shown in FIG. 4, the lobe 150 has a first width adjacent the perimeter 123 and a second width at a terminus adjacent the central space and central axis. The lobes 150 depicted in the figures have a generally curved and convex shape, but it is envisioned that the lobes 150 can have other suitable shapes, such as a terminus with a width greater than or equal to the base or a terminus equal in width to the base. Other shapes of the end region are contemplated to include different transitions from the base to the terminus, including symmetrical, asymmetrical, acute, obtuse, or other suitable means. The at least one lobe 150 may have a convex shape that complements the concave shape of the end plate, along the cephalad or caudal surface. The lobes 150 may have variable thicknesses as well. Furthermore, the at least one lobe 150 may be present on both the top plate 113 and the bottom plate 114. Any number or arrangement of the lobes 150 are contemplated in order to address patients' needs and anatomy.

With this embodiment, the cage 100 is configured so that when the cage 100 is positioned between adjacent vertebrae, the top plate 113 and the bottom plate 114 contact the surface of the vertebral bodies. With increased load on the lobes 150 from the vertebrae on the cage 100, the lobes 150 are capable to flex or bend to absorb or cushion the load on the cage 100. The respective lobes may extend away from the top side 103 and the bottom side 104, so that the lobes 150 contact the vertebral bodies prior to full contact with the perimeter 123 of the top plate 113 and the perimeter 124 of the bottom plate 114. The flexibility of the at least one lobe 150 or the plurality of lobes allows the profile of the implant to complement a vertebral endplate that is not fully concave.

The shape of the lobe 150 may be oriented so that the lobes 150 engage the vertebral body closer to the apophyseal rim, containing cortical bone, rather than the soft central cancellous bone. In an embodiment with multiple lobes 150 on each side 113 114, the load from the adjacent vertebral bodies may be distributed about the total lobes. By spreading the load of adjacent vertebral bodies across at least one lobe 150 in the implant, and preferably a plurality of lobes, the cage 100 reduces the risk of subsidence into the vertebrae and the cancellous bone, by increasing the contact area between the bone and the implant. The overall force against a localized point on the vertebral endplate is spread, and as the lobe flexes, the contact point between the end region 158 and the vertebra is shifted toward the harder cortical bone at the apophyseal rim, supported by the top perimeter 123 and the bottom perimeter 124. Any lobe 150 or combination of lobes 150, may include surface features that encourage bone ingrowth. The features may include pores, ridges, loops, holes, spaces, grooves, or any known surface that increases purchase or grips on the adjacent bone. As the spacer has been packed with cancellous bone graft when the first and second surfaces deflect, they cause the bone graft to support some of the load being transmitted from the adjacent vertebra. In some embodiments, the stiffness of the first and second surfaces, in compression along the axis generally parallel with the perimeter wall, is equal to or less than the compressive modulus of cancellous bone. In accordance with structural mechanics, this situation allows the bone graft to support a significant portion of the spinal load and in accordance with Wolfe's Law facilitates its incorporation into the fusion mass.

The cage 100 may include a plurality of anti-migration features designed to increase the friction between the implant and the adjacent contacting surfaces of the vertebral bodies. Such anti-migration features may include ridges, teeth, lugs, or other purchase-inducing surface treatments. The anti-migration features also stabilize the implant by resisting torsional loads, which might inhibit fusion. As shown in an embodiment of FIGS. 1-7, the cage 10 has grippers 160 functioning as an anti-migration feature. These grippers may be located on a lobe 150 or in various locations on the top and bottom plates 113 114, or generally around the top and bottom perimeters 123 124, or any surface configured to engage adjacent vertebral bodies. The grippers 160 may have a pointed or other engaging geometry to encourage efficient purchase on the vertebral body. The grippers 160 are depicted with a triangular shape with a relatively pointed or sharp gripper terminus. The grippers 160 may be flexible or compressible. The grippers 160 may also be rigid without substantial flexing and may allow for penetration of the vertebral endplate. Penetration of the endplate may allow blood to flow from the cancellous portion of the vertebral body.

The cage 100 may also include additional features to prevent subsidence such as plow edges around the top perimeter 123 and bottom perimeter 124. As best seen in FIG. 1, first 181 and second 182 plow edges are separated by a recess. The first plow edge 181 is adjacent to the top side 103 or bottom side 104 of the top perimeter 123 and bottom perimeter 124. The second plow edge 182 is at a greater distance from the top side 103 or bottom side 104 of the first perimeter 123 and second perimeter 124. The first plow edge 181, the second plow edge 182, and the recess therebetween may extend around the whole perimeter 123 124, or may be broken up, as shown in FIG. 1. The first 181 and second 182 plow edges create additional grip and purchase on the rim of the adjacent vertebral bodies, when the cage 100 is implanted. The recess and plow edges 181 182 allow for additional locations for stabilizing bone ingrowth.

In an embodiment, not shown, a cage 100 may have additional means for engagement with adjacent vertebral bodies. The cage may include a support member (not shown) extending from a top perimeter 123 and/or a bottom perimeter 124. The support member may extend across the top side 103 and/or the bottom side 104. The support member may extend completely across the top side 103 or the bottom side 104 from one side of the top perimeter 123 to another side, and/or one side of the bottom perimeter 124 to another side. The support member may extend from an anterior side 102 to a posterior side 101. The support member may have any viable form or shape, which may include a lobe, a beam, a protrusion, or may be solid within the top 123 or bottom 124 perimeter. The support beam may include an aperture configured to receive a bone anchor or fastener. The bone anchor or fastener may be any know in the prior art, such as a threaded bone screw. The aperture may be centered on the support member, in order to align with a general center of the adjacent vertebral body. The fastener may be inserted from the interior of the cage 100 up through the aperture into the adjacent vertebral body. The fastener may enter the vertebral body within a range of angles from perpendicular to nearly parallel. The fastener may preferably enter the vertebral body within the range of 30 degrees to 65 degrees from vertical. The fastener helps ensure constant contact between the support member, and thus the cage 100, which limits motion at the implant-bone interface. The preferred range of insertion, between 30-65 degrees, adds to the resistance of forward bending of the fastener and increases the prevention of implant kick-out. The angle may be variable for each cage 100; the angle may be determined by a drill guide or other tool.

In an embodiment of a relatively large cage 100, a fastener may be secured through a support member on the top side 103 and the bottom side 104. The relatively large size of the cage allows access to a head or driving portion of one or two fasteners, without interfering with each other.

In an embodiment of a relatively small cage 100, a single fastener may be used to secure only one support member to an adjacent vertebral body. The head of the single fastener may be accessed from the side of the cage 100 opposite from the side having the support member. For example, a small cervical cage may have a support member with an aperture only on the superior or top 103 side, extending from the top perimeter 123. The cage 100, in this embodiment, may be asymmetric regarding the top 103 and the bottom side 104. The fastener passes through the aperture at a preferred angle and secures into the adjacent vertebral body. Because of the relatively small size of the cage 100, access to the head of the fastener may be through the opposite, or bottom side 124, of the cage.

The fasteners may be deployed independently from the cage 100. The embodiment does not require any mechanism to translate non-parallel turning force to the fastener, such as a universal joint, worm drive, or other hardware. The absence of additional mechanisms within the cage 100 allows for space that may be packed with grafts or other bony material.

Figure 6A:
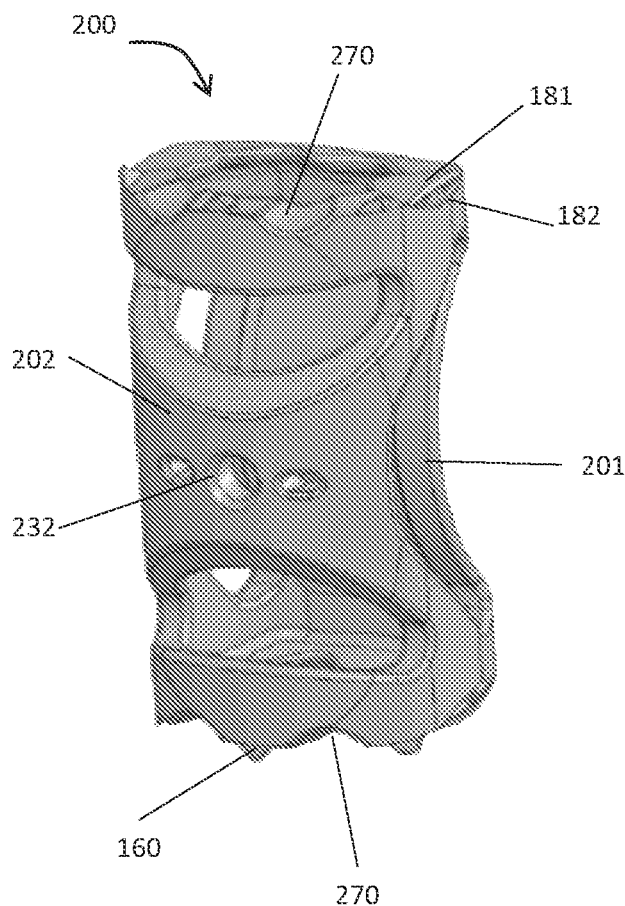
FIG. 6A shows an anterior perspective of a cervical cage with divots.
Figure 6B:
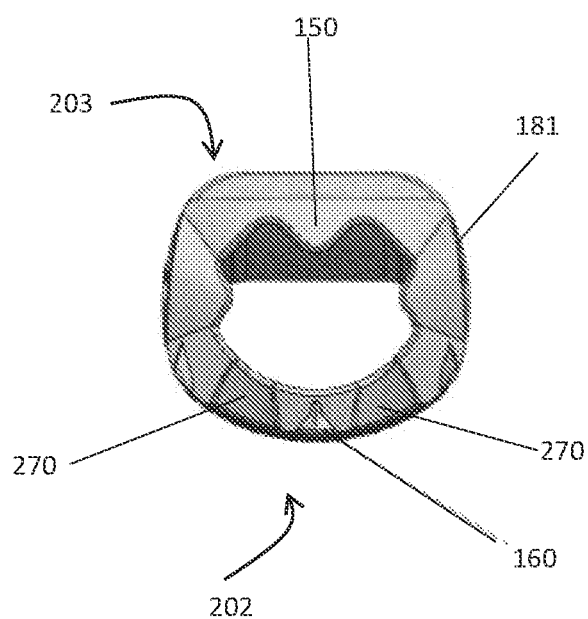
FIG. 6B shows a top view of a cervical cage with divots.

An embodiment of a cervical cage 200 is shown in FIGS. 6A and 6B with additional features to assist in fixing the cage 200 between vertebral bodies. Similar to the cage 100 in FIGS. 1-5, the cage 200 has a flexible or compressible posterior plate 210 on a posterior side 201 of the cage 200. Opposite the posterior plate 210 is an anterior plate 212 on the anterior side 202 of the cage 200. The posterior plate 210 may have any of the configurations or dimensions discussed above as related to cage 100, allowing the posterior side 201 of the cage 200 to reduce in size relative to the anterior side 202. In addition to lobes 150, grippers 160, and plow edges 181 182, cage 200 depicts divots 270 in the top and bottom plates 113 114. The divots 270 create a space generally through the perimeters 123 124 of the cage 200. As shown in FIG. 6B, the divots 270 allow for the passage of screws (not shown) through the anterior side 102 of top side 103 and bottom side 104 of the cage 200. The divots are intended to be suitable for use with locking plates and screws, known in the prior art as in U.S. Patent Publication 2020/0155327; U.S. Patent Publication 2020/0205993; U.S. Pat. Nos. 9,526,620; 8,801,785; 8,268,000; and 7,220,263; all of which are incorporated herein by reference. In practice, the cage 200 would be combined with an anterior locking plate using screws that pass through the perimeter 123 124 of the cage 200 and into the adjacent vertebral bodies.

In addition to the divots 270, the cage 200 may also include anterior connection elements 232, which may be configured to secure a locking plate to the cage 200. The anterior connection elements may be a threaded or non-threaded aperture or apertures (as shown in FIG. 6A), a threaded or unthreaded bus extending from the anterior plate 212 or anterior side 202, or any other suitable feature allowing for securing or manipulation of the cage 200. The anterior connection elements may be used as a connection element for an inserter or other tool.

The present disclosure is also intended to include other configurations which allow the posterior side of the cage to compress or translate relative to the anterior side. The displacement or movement of the posterior side may be consistent with the amount of load placed on the cage 100. After fusion, which may occur 3-6 months after surgical implantation, the anterior plate 112 fixation prevents kick-out of the implant. Kick-out prevention is key to avoid temporary paralysis of the patient, if the cage 100 moves and contacts surrounding nerves or the spinal cord.

One embodiment 300 is depicted in FIGS. 7A and 7B. Similar to cage 100, cage 300 has top 103 and bottom 104 sides, with top 113 and bottom plates 114, anterior side 102 with an anterior plate 112. The cage 300 has securing elements such as lobes 150, grippers 160, and plow edges 181 182. The cage 300 may also have anterior apertures 331 and side apertures 130, and connection elements 332, any of which may be used to manipulation, connection, or bone ingrowth. The cage 300 may also include lateral edge apertures 333 which may also affect weight of the cage 300 or additional lateral compression of the cage 300, after implantation. Cage 300, however, depicts an alternative posterior plate providing an alternative means of posterior cage 300 compression. Cage 300 has a posterior first section 316 and a posterior second section 317, which engage at a hinge 315. The hinge 315 allows for anterior displacement of the posterior first section 316 and the posterior second section 317. As force is applied to the posterior sides of the top 113 and bottom 114 plates the hinge allows for relative movement of the adjacent portions of the posterior first 316 and posterior second 317 sections.

FIGS. 7A and 7B show a configuration where the hinge 315 translates toward the anterior plate 112 during posterior compression of the cage 300. The hinge 315 may be configured so that the posterior first 316 and posterior second 317 are a unitary or monolithic construction, or the hinge may be open, such that the posterior first 316 and posterior second 317 sections are separate elements that engage each other at the hinge 315. In a non-compressed state of the cage 300, the posterior first 316 and posterior second 317 sections may contact one another, or they may be separated by a distance. The cage 300 may also include stop elements which prevent the posterior first 316 and posterior second 317 sections from displacing more than a desired distance. The posterior first 316 and the posterior second 317 sections may have a non-compressed orientation in which they 316 317 generally align with the posterior plane or they may be oblique to the posterior plane.

Figure 8A:
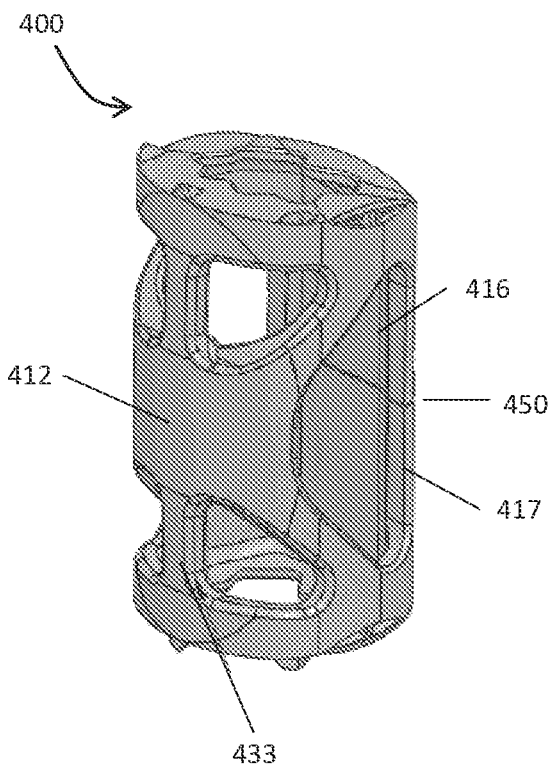
FIG. 8A shows a side anterior perspective of a cervical cage with an anterior stabilizer.

FIGS. 8A-8E show alternative configurations of the cervical cage. The embodiment 400 in FIG. 8A has an anterior plate 412 separating a first perimeter 123 and a second perimeter 124. The anterior plate 412 is connected to the perimeters via an anterior support 433. The anterior support 433 may act to stabilize the anterior side of the cage and add rigidity to the top 113 and bottom plates 114. The posterior plate has a posterior first section 416 and a posterior second section 417. The first 416 and second 417 sections come together at a junction 450. The junction 450 allows for displacement of the posterior first section 416 and the posterior second section 417 generally toward each other. As force is applied to the posterior sides of the top 113 and bottom 114 plates the junction 450 allows for a limited displacement or movement of the adjacent portions of the posterior first 416 and posterior second 417 sections. The junction 450 may be designed to have, or be, a specific gap separating the first 416 and second 417 sections. The gap may be less than 1 mm, between 1 mm and 2 mm, 2 mm, between 2 mm and 3 mm, 3 mm, between 3 mm and 4 mm, 4 mm, between 4 mm and 5 mm, or greater than 5 mm, depending on the requirements of the patient's anatomy. The junction 450 allows for a maximum posterior compression of the cage, which is then stopped by the engagement and abutment of the first 416 and second 417 sections. The junction 450, as shown in FIG. 8A is not configured for an anterior-posterior displacement, as is possible with the hinge 315 in other embodiments of the cage.

The junction 450 may include additional elements located on either the first 416 or second 417 sections to assist in alignment of the ends of the sections 416 417. For example, the top edge of the second section 417 may have a recess into which the lower edge of the first section 416 engages. The recess prevents slippage or overlapping of the edges of the first 416 and second 417 sections and helps ensure that any posterior compression of the cage is stopped at the intended limit, as set by the gap in the junction 450. The recess may be on either of the sections 416 417. The recess may be of any shape or construction that prevents unintended movement of the first 416 or second 417 sections. In some embodiments, the junction 450 may not be open, but rather a material or substance different than the material of the first 416 and second 417 sections. The junction 450 may be made of a resilient or shock absorbent material in order to allow only a certain amount of displacement or travel of the first 416 and second 417 sections.

Figure 8B:
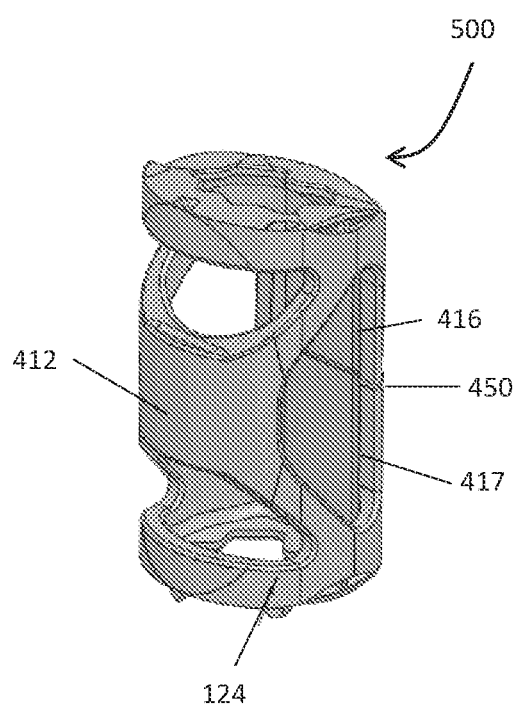
FIG. 8B shows a side anterior perspective of a cervical cage with a gapped posterior.

FIG. 8B shows an embodiment 500 of a cage which may include a junction 450 as described in relation to FIG. 8A. Embodiment 500 omits anterior support between the upper 123 and lower 124 perimeters; however, the anterior support 433 may link only one of the upper 123 or lower 124 perimeters to the anterior plate 412. It is also contemplated that the anterior supports 433 may take any other form or shape to adequately provide support for the anterior side 102 of the cage 500. It is further contemplated that the anterior support 433 is constructed of the same material as the cage 500. The anterior support 433 may be tuned to provide different amounts of resistance to compressions relative to other parts of the cage 500. For example, the anterior support 433 may be made of the same material as the cage 500, but in a thicker or thinner cross section, or having a different density. The anterior support 433 may also be made of a different material than the cage 500, such as a polymer (i.e., PETE, PET, HDPE, LDPE), a different alloy or Nitinol, or other placeable or printable material, in order to provide a compressibility or resistance different than other parts of the cage 500.

Figure 8C:
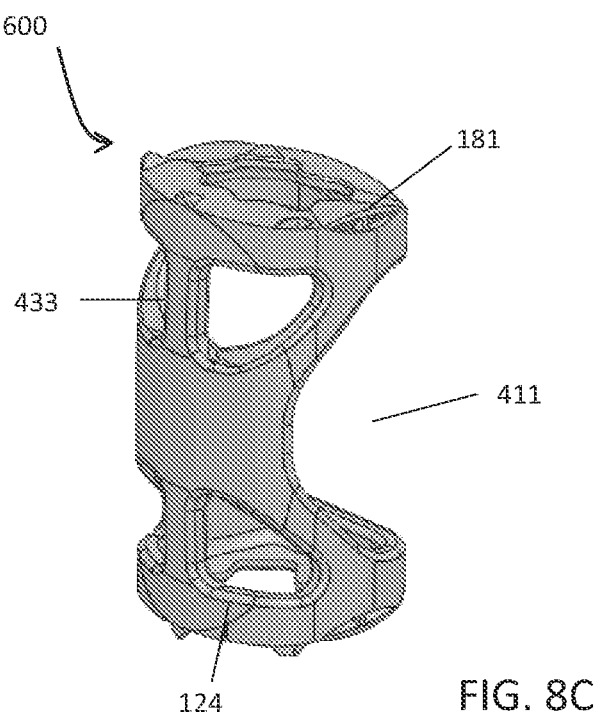
FIG. 8C shows a side anterior perspective of a cervical cage with an open posterior.

FIG. 8C shows an embodiment 600 of the cervical cage without a posterior plate 110, rather the cage 600 has an open posterior side 411. This embodiment allows for an additional variation of compressibility of the cage 600, and particularly the posterior side. As described in relation to cages 400 and 500, anterior supports 433 and side supports 133 may provide functional resistance to the divergence of the anterior sides of the upper 123 and lower 124 perimeters, which may occur with a limited or absence of posterior compression or translational movement.

Figure 8D:
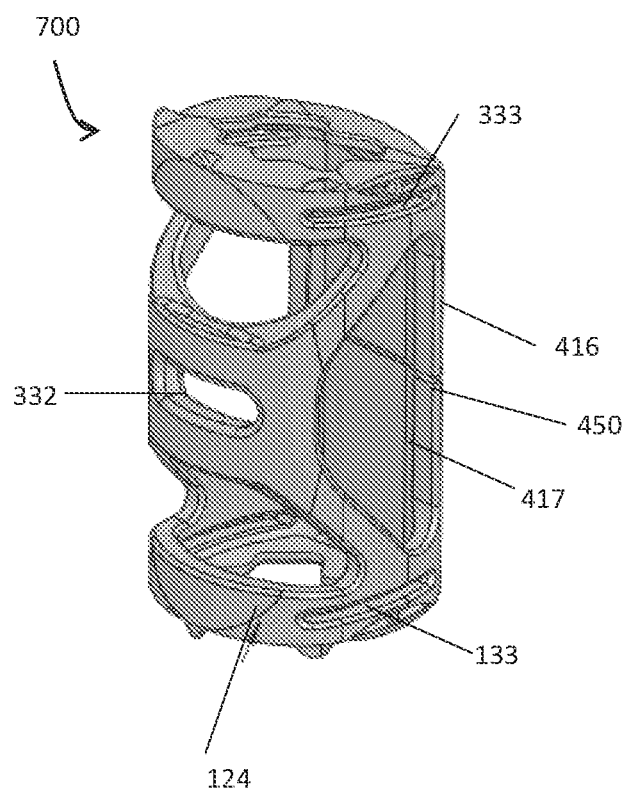
FIG. 8D shows a side anterior perspective of a cervical cage with a gapped posterior and connection elements.

FIG. 8D shows an embodiment 700 of a cervical cage with first 416 and second 417 sections separated by a junction 450. The embodiment 700 has an anterior plate 412 with at least one connection element 332. The connection elements 332 be apertures for attachment screws or other attachment means. The connection element 332 may be smooth, textured, or threaded. The connection element also provides an opportunity for some bone in-growth.

Figure 8E:
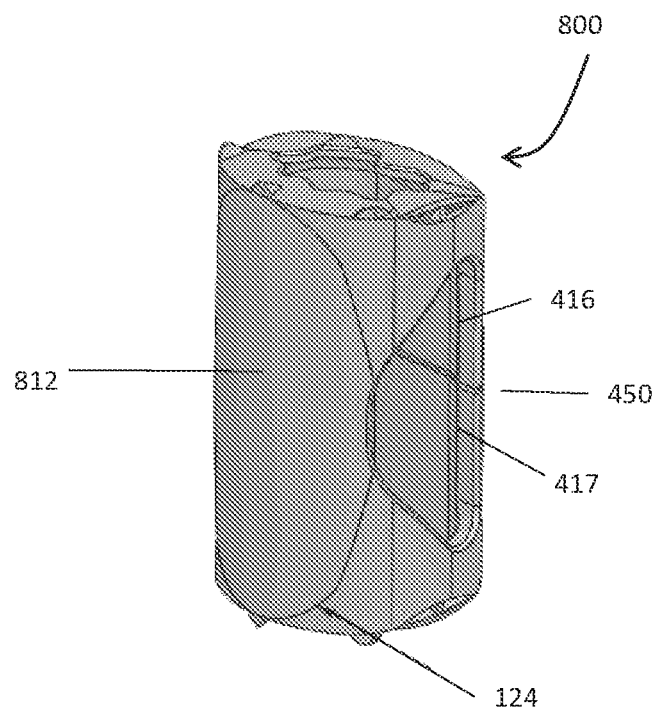
FIG. 8E shows a side anterior perspective of a cervical cage with a solid anterior.

FIG. 8E shows an embodiment 800 of a cervical cage with first 416 and second 417 sections separated by a junction 450. Cage 800 has a solid anterior plate 812 spanning between a first perimeter 123 and a second perimeter 124. The solid anterior plate may provide a more robust anterior side of the cage 800 that prevents any anterior displacement of the cage 800, and directing any compression of the cage to the posterior side, to be absorbed by the junction 450.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

Any methods disclosed herein comprise one or more steps or actions for performing the described method. The method steps and/or actions may be interchanged with one another and applicable to all embodiments of the intervertebral body implants described herein. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

The invention claimed is:

1. A cervical cage comprising:
 a superior end plate, having a superior anterior side and a superior posterior side, and a superior perimeter connecting the superior anterior side and the superior posterior side;
 an inferior end plate, having an inferior anterior side and an inferior posterior side, and an inferior perimeter connecting the inferior anterior side and the inferior posterior side,
  wherein the superior end plate and the inferior end plate define a central region therebetween, the central region further defined by:
   an anterior plane extending between the superior anterior side and the inferior anterior side,
   a posterior plane extending between the superior posterior side and the inferior posterior side, and
   a longitudinal axis extending through the central region between the superior end plate and the inferior end plate;
 an anterior support, with a first rigidity, connecting the superior end plate and the inferior end plate;
 a posterior support, with a second rigidity, connecting the superior end plate and the inferior end plate at posterior edges; and
 wherein the first rigidity is greater than the second rigidity, such that the posterior support can transition toward the longitudinal axis.

2. The cervical cage of claim 1, wherein the posterior support further comprises:
 a superior end connected to the superior posterior side on the posterior plane; an inferior end connected to the inferior posterior side on the posterior plane; and an extension between the superior end and the inferior end.

3. The cervical cage of claim 2, wherein the extension deviates from the posterior plane.

4. The cervical cage of claim 3, wherein the extension can deviate anteriorly from the posterior plane.

5. The cervical cage of claim 3, wherein the extension can deviate posteriorly from the posterior plane.

6. The cervical cage of claim 3, wherein the extension has at least one apex.

7. The cervical cage of claim 3 wherein the extension is curved.

8. The cervical cage of claim 6, wherein the at least one apex may be located anywhere in the central region.

9. The cervical cage of claim 8, wherein the at least one apex may be positioned closer to the longitudinal axis than the posterior plane, or the at least one apex may be positioned closer to the posterior plane than the longitudinal axis.

10. The cervical cage of claim 8, wherein the at least one apex may be positioned closer to the superior end plate than the inferior end plate, or the at least one apex may be positioned closer to the inferior end plate than the superior end plate.

11. The cervical cage of claim 1, wherein the superior end plate comprises at least one recess and/or the inferior end plate comprises at least one recess.

12. A spinal implant comprising:
 a caudal portion, having a caudal anterior side and a caudal posterior side, and a caudal perimeter connecting the caudal anterior side and the caudal posterior side;
 a cephalad portion, having a cephalad anterior side and a cephalad posterior side, and a cephalad perimeter connecting the cephalad anterior side and the cephalad posterior side;
 wherein the caudal portion and cephalad portion define an intermediate region therebetween and having a longitudinal axis and are connected by a first anterior wall and a second posterior wall, the first wall having a greater rigidity than the second wall;
 wherein the caudal anterior side and the cephalad anterior side are separated by an anterior distance along an anterior plane and the caudal posterior side and the cephalad anterior side are separated by a posterior distance along a posterior plane; and
 wherein the second wall is configured for a preferential movement between the cephalad and caudal portions, wherein the preferential movement is toward the longitudinal axis.

13. The spinal implant of claim 12, wherein the preferential movement reduces the posterior distance.

14. The spinal implant of claim 13, wherein the second wall extends between the caudal posterior side and the cephalad posterior side anteriorly to the posterior plane.

15. The spinal implant of claim 13, wherein the second wall extends between the caudal posterior side and the cephalad posterior side posteriorly to the posterior plane.

16. The spinal implant of claim 13, wherein the second wall extends between the caudal posterior side and the cephalad posterior side anteriorly and posteriorly to the posterior plane.

17. A spinal implant comprising:
 a superior end plate, having an anterior side and a posterior side, and a superior perimeter connecting the anterior side and the posterior side;
 an inferior end plate, having an anterior side and a posterior side, and a perimeter connecting the anterior side and the posterior side;
 wherein the superior end plate and the inferior end plate define a central region therebetween and having a longitudinal axis, further defined by an anterior plane and a posterior plane extending between each of the anterior and posterior sides;
 an anterior support connecting the superior and inferior end plates; and
 a posterior support, less rigid than the anterior support, connecting the superior and inferior end plates, wherein the posterior support has a greater flexibility than the anterior support, and the posterior support is configured to move toward the longitudinal axis.

18. The spinal implant of claim 17, wherein when the posterior support flexes, the posterior support posteriorly traverses, away from the anterior support, a posterior plane extending between the superior end plate and the inferior end plate.

19. The spinal implant of claim 17, wherein when the posterior support flexes, the posterior support anteriorly traverses, toward the anterior support, a posterior plane extending between the superior end plate and the inferior end plate.

20. The spinal implant of claim 17, wherein when the posterior support flexes, the posterior support anteriorly and posteriorly traverses a posterior plane extending between the superior end plate and the inferior end plate.

\* \* \* \* \*